Figure 1:
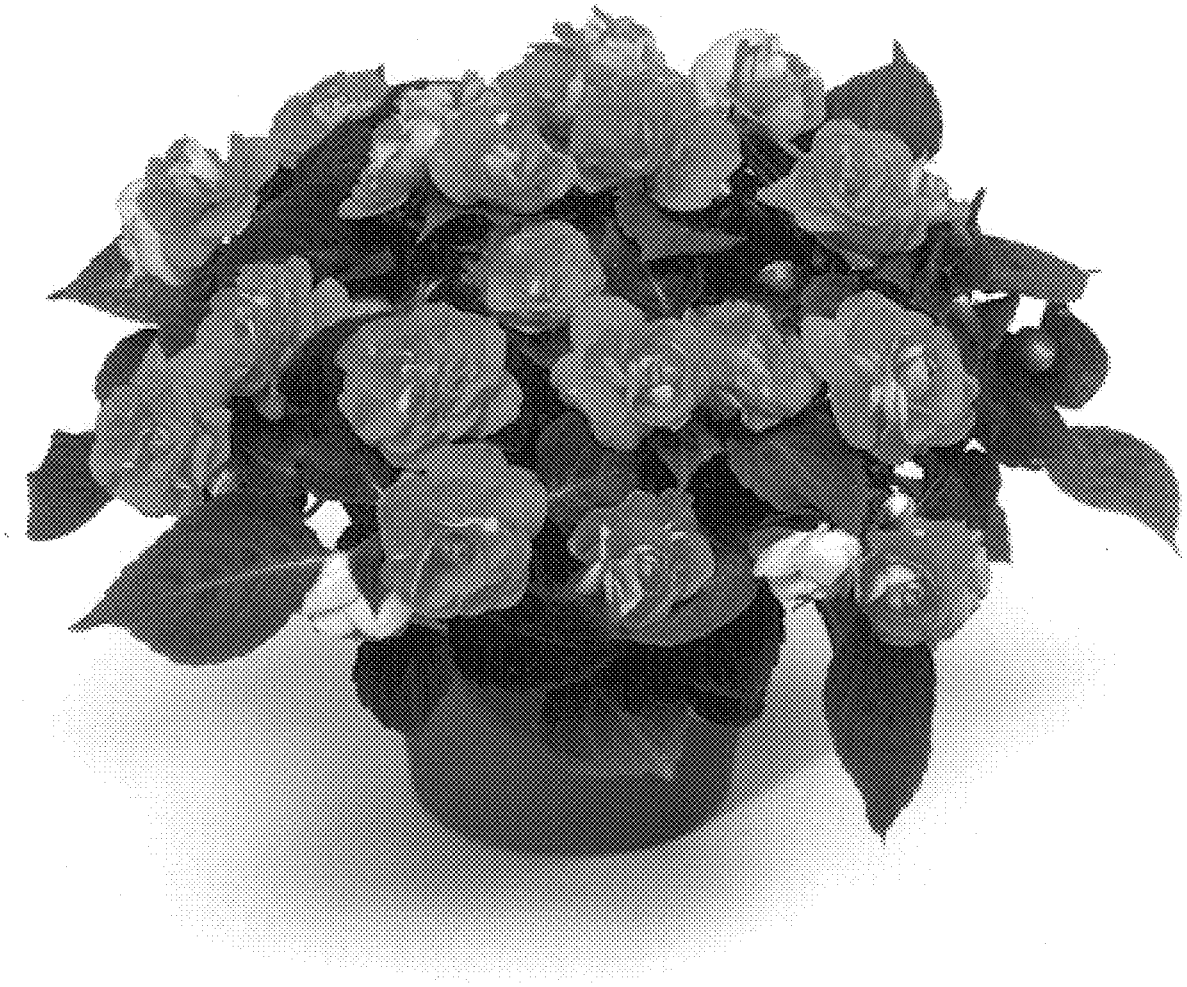

US00PP11487P

United States Patent [19]

Jonkers

[11] Patent Number: Plant 11,487

[45] Date of Patent: Aug. 22, 2000

[54] IMPATIENS PLANT NAMED 'DIDI CARMINE'

[75] Inventor: J. B. (Hanneke) Jonkers, Hoorn, Netherlands

[73] Assignee: Goldsmith Plants, Inc., Gilroy, Calif.

[21] Appl. No.: 09/123,411

[22] Filed: Jul. 28, 1998

[51] Int. Cl.[7] ..... A01H 5/00

[52] U.S. Cl. ..... Plt./317

[58] Field of Search ..... Plt./317

[56] References Cited

PUBLICATIONS

GTITM UPOVROM Citation for 'Didi Carmine' as Per QZ PBR 971001; Sep. 16, 1997.

*Primary Examiner*—Howard J. Locker
*Assistant Examiner*—Kent L. Bell
*Attorney, Agent, or Firm*—Rothwell, Figg, Ernst & Kurz

[57] ABSTRACT

A new and distinct cultivar of Impatiens plant, and named 'Didi Carmine' is provided. 'Didi Carmine' is distinct in its carmine colored fully double flowers, its early and free flowering, and its basal branched, compact growth habit.

1 Drawing Sheet

BACKGROUND OF THE NEW PLANT

The present invention comprises a new and distinct cultivar of impatiens, botanically known as *Impatiens walleriana,* and hereinafter reffered to by the cultivar name 'Didi Carmine', and is characterized by the following combinations of repeatedly observed traits:

1. Fully double flowers,
2. early flowering,
3. compact basal branching, and
4. free flowering.

Asexual reproduction of this cultivar by stem cuttings taken during November, 1996, at Andijk, The Netherlands, has demonstrated that the characteristics of the new cultivar as herein described are firmly fixed and are retained through successive generations of such asexual propagation, such reproduction establishing that the plant does in fact maintain the characteristics described in successive generations. The female parent (i.e., the seed parent) was an Impatiens walleriana named IN-1791-1 (unpatented) and the male parent (i.e., pollen parent) was an Impatiens walleriana named IN-1789-8 (unpatented). The cross was made in 1995 and the seedling was selected in 1996.

This new cultivar has been identified as Impatiens 'Didi Carmine'. It is possible that other identification will be adopted in the trade, but the name selected will serve for the purpose hereof.

DESCRIPTION OF THE PHOTOGRAPH

This new impatiens plant is illustrated by the accompanying photographic drawing which shows blooms, buds, and foliage of the plant in full color, the colors shown being as true as can be reasonably obtained by conventional photographic procedures.

FIG. 1 shows overall plant habit;

DESCRIPTION OF THE NEW CULTIVAR

The following observations and measurements describe plants grown outside in the field in Andijk, The Netherlands. Measurements were recorded in August, 1997, on plants approximately 14 weeks old. Fully developed organs were used for measurements and color desscriptions, unless otherwise indicated. Color references are made to The R.H.S. Colour Chart of The Royal Horticultural Society, London, England, except where general color terms of ordinary significance are used.

'Didi Carmine' has not been observed under all possible environmental conditions. The phenotype may vary with variations in environment and horticultural practices, such as temperature, light intensity, day length, fertilization and propagation procedure, without any change in genotype.

Parentage:

*Female parent.*—Impatiens walleriana IN-1791-1 (unpatented).

*Male parent.*—Imapatiens walleriana IN-1789-8 (unpatented).

Propagation:

*Type cutting.*—Stem (internodal) cutting with two nodes and attached leaves.

*Time to initiate roots.*—10–14 days at 70–75 degrees F with a fully developed root mass at 21 days.

*Rooting habit.*—Fibrous, branching, adventitious root system.

Plant description:

*Form.*—Upright.

*Growth habit.*—Upright branching plant habit with upper leaves and flowers produced in whorls. When grown in a 4 inch pot for 10–12 weeks the height is approximately 4–5 inches and the width is approximately 5 inches.

*Foliage description.*—Leaves are simple. Lower leaf arrangement is alternate with upper leaves arranged in whorls of 5. Leaf shape is ovate with acute apex and acute base. Leaf size is 4.5 cm×3 cm. Leaf margin is crenate with ciliation. Leaf surface is glabrous. Leaf color is green. The upper surface is yellow-green group 147A. Under surface is yellow-green group 147B. Venation is pinnate.

*Petiole.*—Petiole length is 2 cm; and diameter is 0.2 cm; Color is yellow-green 147C.

Flower description:

*Flowering habit.*—Rooted cutting to full flowering plant in seven weeks. Indeterminate, flowering continuously. Flowers develop in the upper leaf axils.

*Natural flowering season.*—Flowers continuously throughout the year.

*Flowers borne.*—On pedicels which are yellow-green 145C and 3 cm long in clusters of 2–7 flowers with a peduncle color of yellow-green 145C and length of 2 cm long.

*Spur*.—Short spurred; length is 3.5 cm; color is 147C.

*Buds*.—Buds are oval-shaped at first color 55A and 145B; size is 1.7 cm×1.3 cm.

*Quantity of flowers*.—Floriferous. Each auxiliary cluster of 2–7 flowers developing progressively from the leaf whorls so that buds as well as mature flowers are visible at the same time in large numbers.

*Petals*.—Number of petals 35, with all petals overlapping. Outer petals average 2.5 cm length×2.2 cm width and inner petals average 1.3 cm length×1.1 cm. width. All petals are slightly cupped.

*Flower color*.—Upper surface: Red-purple group 57A. Lower surface: Red-purple group 58D.

*Flower size*.—Approximately 4 cm wide and 4 cm long.

*Nectary length*.—Approximately 2 cm long.

*Reproductive organs*.—No reproductive organs.

DISEASE AND INSECT RESISTANCE

No known susceptibility to diseases or insects noted to date.

COMPARISON WITH THE KNOWN CULTIVARS

When 'Didi Carmine' is compared to Impatiens 'Fiesta Lavender Orchid' (unpatented), it is found that 'Didi Carmine' exhibits a more vigorous plant habit and is also more floriferous.

When 'Didi Carmine' is compared to 'IN-1791-1' and 'IN-1789-8', the parental cultivars, the instant cultivar has double flowers and the parental cultivars are both single flowering.

I claim:

1. A new and distinct cultivar of Impatiens plant named 'Didi Carmine', substantially as described and illustrated herein, characterized particularly as to novelty by its fully double carmine colored flowers, its early and free flowering, and its basal branched, compact growth habit.

* * * * *